United States Patent [19]
Tracy et al.

[11] Patent Number: 6,057,463
[45] Date of Patent: May 2, 2000

[54] N-ACYLAMINOALKANE SULFONATE AND AMPHOTERIC SURFACTANT BLENDS AND METHODS FOR PREPARING THE SAME

[75] Inventors: David James Tracy, Plainsboro; Paul Frank D'Angelo, Princeton, both of N.J.

[73] Assignee: Rhodia Inc., Cranbury, N.J.

[21] Appl. No.: 08/641,121

[22] Filed: Apr. 30, 1996

[51] Int. Cl.$^7$ .................................................. C07C 231/00
[52] U.S. Cl. .................................................. 554/49; 554/68
[58] Field of Search .......................................... 554/49, 68

[56] References Cited

U.S. PATENT DOCUMENTS 4,515,721   5/1985   Login et al. .............................. 554/92
5,496,959   3/1996   Day ........................................... 554/69

OTHER PUBLICATIONS

Derwent abstr. of JP–05–222,395,93–309,382, 1993.

*Primary Examiner*—Deborah D. Carr
*Attorney, Agent, or Firm*—John Daniel Wood

[57] ABSTRACT

Blends of N-acyl aminoalkane sulfonates and amphoteric and/or anionic surfactants can be prepared by quenching a molten reaction mixture of an aminoalkane sulfonate amidated with a fatty acid with an aqueous solution comprising an amphoteric and/or anionic surfactant.

N—acyl aminoalkane sulfonates can be purified by quenching a molten reaction mixture in isopropanol.

41 Claims, No Drawings

6,057,463

N-ACYLAMINOALKANE SULFONATE AND AMPHOTERIC SURFACTANT BLENDS AND METHODS FOR PREPARING THE SAME

The present invention relates to an improved process for preparing purified N-acyl aminoalkane sulfonates. The present invention also relates to an improved process for preparing blends of N-acyl aminoalkane sulfonates and amphoteric and/or anionic surfactants.

BACKGROUND OF THE PRESENT INVENTION

Acyl taurinates and acyl isethionates, broadly classed as acyl aminoalkane sulfonates and acyloxyalkane sulfonates respectively, are known ingredients useful in synthetic detergent bars (syndet bars), shampoos, bubble baths, body washes, creams and lotions.

The reaction of acid chlorides of carboxylic acids with 2-amino- or 2-hydroxyalkanesulfonic acids and their alkali metal salts to yield anionic surfactants (for example, sodium N-acyltaurates and sodium acylisethionates, respectively) is well known as the Schotten-Baumann synthesis.

The Schotten-Baumann chemistry is very laborious and costly, requiring the handling of hazardous raw materials such as phosphorus trichloride and intermediates like acid chlorides as well as wastes like phosphorus acid. Large quantities of waste products are generated as a result of this chemistry. Also, the finished products contain significant amounts of sodium chloride as an undesirable by-product. The removal of the sodium chloride is possible, but expensive.

Sodium acyl aminoalkane sulfonate synthesis has been greatly improved by the direct amidation of sodium taurinate with fatty acids or by reacting a fatty amide with a sodium isethionate. This direct esterification route is cost-effective and these products are suitable for use in commercial toilet soap preparations.

The preparation of such sulfonates by direct amidation of an aminoalkane sulfonate with a fatty acid has presented difficulties because of the high temperature required to obtain suitable conversion. At temperatures required for direct acylation, usually in the range of 180° to 250° C., the molten reaction product rapidly degrades in color and loses activity. It has been found necessary to rapidly cool the reaction mass in order to obtain a final product.

PCT publication WO 95/18095 teaches preparing a taurinate by direct acylation, chilling the reaction mixture on a plate, redissolving the solid reaction mixture in lower alkanols or ketones under reflux followed by cooling to separate the insoluble product from the byproducts and solvent.

U.S. Pat. No. 2,697,872 teaches acylating a sodium N-methyl taurine with molten fatty acid anhydride in the absence of catalyst. The reaction generally is conducted at 1000 to 200° F. (though higher temperatures are mentioned generically). At some temperature acetone is added and the mixture cooled to 60° F. to isolate a purified product. It is noted that the acetone is added to the reaction mixture so that one would presume that the reaction mixture is not being quenched from an elevated temperature.

U.S. Pat. No. 3,429,136 teaches that in preparing acyl isethionates by direct esterification, the molten reaction mass can be cooled by injecting cold water directly into the molten crude reaction mixture to cool the mass by evaporative cooling below a temperature at which rapid discoloration would occur and this can be done without causing appreciable hydrolysis of the ester.

Since this crude reaction product ordinarily contains unreacted fatty acid, sulfonate or both, various methods have been proposed for purification. Generally these methods comprise forming liquid systems in which the impurities are soluble and the product is insoluble. Following cooling, the soluble impurities separated with the liquid by filtration means.

U.S. Pat. No. 4,515,721 teaches that excess fatty acid can be removed from an isethionate reaction mixture by quenching the hot crude fatty acid ester by immersion in a liquid in which the desired ester product is insoluble and the unreacted fatty acid soluble. The phases are separated to affect purification. In this patent the isethionate can be quenched in various products including lower chain length alcohols, fatty alcohols, fatty alcohol ethoxylates, polyethylene glycols, polyoxyalkylene derivatives of polyethylene glycol, fatty triglycerides, fatty esters and fatty amides. The preferable quenching liquid is isopropanol.

U.S. Pat. No. 4,612,132 describes a process for preparing an aqueous surfactant solution and gel of an acyloxyalkane sulfonate salt by combining the sulfonate salt with a water soluble polyol and water. This mixture is heated above the boiling point of water under super atmospheric pressure to form a reversible solid colloidal solution from which the product can then be recovered. See also, U.S. Pat. No. 4,696,767.

U.S. Pat. No. 5,415,810 discloses that blends of SCI and betaine (zwitterioncs) can be made in an aqueous system where the zwitterionic surfactant assists in the dissolution of the isethionate.

It is known to prepare blends of surfactants to accomplish various desired end results. Blends of isethionates and betaines, optionally with soap, are known for producing syndet bars (U.S. Pat. No. 5,372,751).

Presently, blends of taurinates and betaines are made by dissolving or slurrying the taurinate in a heated (400° C.) aqueous betaine solution. This procedure requires the preparation of solid taurinate and the reheating of the betaine solution.

It is an object of the invention to prepare a high active content, substantially salt free acyl taurinate by a process which eliminates the steps of solidification and reslurrying. The present process is thereby more economical because the quenching operation is faster than the flaking operation insuring lower decomposition of product during manufacture.

It is also an object of the invention to prepare blends of taurinates with amphoteric and/or anionic surfactants, optionally with other ingredients and surfactants in a process which eliminates the need for solidifying and reslurrying the taurinate, reduces product decomposition, thereby making the product in a more economical manner.

SUMMARY OF THE INVENTION

In accordance with the invention, acyl taurinates can be effectively purified by directly reacting taurinate salts with a fatty acid or fatty acid ester or a hydroxyalkane sulfonate with a fatty acid amide at elevated temperature sufficient to effectively amidate without excessive product decomposition (from about 180° to about 2500° C.) followed by quenching the molten reaction mixture in a lower molecule weight alcohol or ketone. The product separates as a solid and is removed by centrifugation or filtration or other appropriate solid separation techniques. The product can be used as is or further washed.

Another embodiment of the invention includes quenching the molten acyl taurinate prepared as above in an aqueous solution of amphoteric and/or anionic surfactant optionally including other ingredients and/or surfactants. This allows for the convenient preparation of taurinate/amphoteric and/or anionic surfactant blends while avoiding the solidification, classification, and reslurrying techniques required presently. The product can be a viscous liquid or paste depending on solids concentration.

DETAILED DESCRIPTION OF THE INVENTION

The embodiments of the invention proceed from a molten reaction mixture of an N-acyl aminoalkane sulfonate preferably prepared by reacting an aminoalkane sulfonate with a fatty acid or fatty acid ester. Alternatively, the N-acyl aminoalkane sulfonate can be prepared by reacting a hydoxyalkane sulfonate with a fatty acid amide.

The N-acyl aminoalkane sulfonates can be represented by the formula

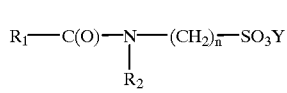

Formula I wherein $R_1$ is a hydrocarbyl radical, desirably from about 6 to about 26 carbon atoms, $R_2$ represents hydrogen, methyl or cyclohexyl, n is integer of from 2 to 4, preferably 2 and Y is an alkali metal or alkaline earth metal, more particularly, sodium, potassium, lithium or magnesium and preferably sodium. The alkane portion of the sulfonate detergents of Formula I for use herein includes ethylene and branched or unbranched propylene or butylene. The fatty acyl moiety is a hydrocarbyl radical containing from about 6 to about 26 and preferably from about 6 to about 20 carbon atoms such as hexanoic, octanoic, decanoic, dodecanoic, lauric, behenic, palmitic, stearic, myristic, arachidic, oleic, linolenic, linoleic, and the like including mixtures of the foregoing as in the particularly preferred cocoyl derivatives from coconut oil fatty acids. Fatty acids from natural sources are comprised of numerous fatty acids whose chain lengths generally all fall within the stated carbon range. A small proportion of mono- or di-unsaturated fatty acid derivatives may be desirable to provide adequate foaming and solubility in blends containing the neat soap. Normally, the degree of unsaturation will not be less than about 2 or more than 12, when measured by iodine number. It will be observed in this context that the term "hydrocarbyl" is intended to embrace linear and branched aliphatic radicals that include alkyl, alkenyl alkynyl, and alkadienyl moieties. Too large a proportion of unsaturation, tends to render the sulfonate susceptible to oxidative degradation. The preferred compounds are N-methyl taurinates wherein $R_2$ represents methyl and n is an integer of 2. Preferably, $R_1$ represents cocoyl or oleyl, and M is an alkali or alkaline earth metal, preferably sodium.

Compounds of Formula I can be prepared by the direct amidation of an aminoalkane sulfonic acid of Formula II.

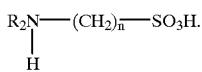

Formula II with a fatty acid of Formula III

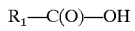

Formula III wherein $R_2$, n and $R_1$ are as previously defined.

The componds of Formula I can also be prepared by amidating a hydroxyalkane sulfonate of the formula:

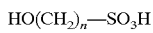

Formula IV with a fatty acid amide of Formula V

Formula V

The amidation is generally conducted at an elevated temperature sufficient to effect reaction but insufficient to cause product degradation, generally above 180° C. to about 250° C. (temperatures of about 195° C.–about 200° C. being preferred if the reaction mixture can be kept molten) in the presence of catalytic amounts of boric acid and/or zinc or magnesium oxide. Temperatures above the decomposition point can be handled by incorporating scrubber to purify the area. The addition of viscosity modifiers such as paraffin wax can lower the viscosity so that more complete condensation can be achieved. The reaction is conducted for a period of time sufficient to achieve conversion but insufficient to allow substantial product degradation, for example from about 1 to about 10 hours.

Conversion to acyltaurinate is monitored by decreasing acid number and increasing anionic activity based on two-phase methylene blue titration. The analytical techniques used for monitoring the progress of the reaction include titrimetric and gas chromatographic analyses well known by those skilled in the art to trace the decrease in fatty acid content of the mixture and the increase in the taurate content as the reaction progresses toward completion. (For examples of such analytical techniques see *Detergent Analysis—A Handbook for Cost-Effective Quality Control*, by E. M. Milwidsky and D. M. Gabriel (George Goodwin, London, 1982) incorporated by reference herein in its entirety, especially at pages 119–120, 133–134, and 255.

Products from said reactions can be used to manufacture a number of personal cleansing formulations (e.g., bar soap, shampoos, body washes, etc.).

In accordance with the invention, the molten reaction product is quenched in an aqueous solution of amphoteric and/or anionic surfactant at a rate sufficient to cool the reaction mass below degradation temperature.

Amphoteric/Zwitterionic Surfactants

Amphoteric surfactants useful in the invention can broadly be described as a surface active agent containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants can be broadly described as surface active agents having a positive and negative charge in the same molecule which molecule is zwitterionic at all pHs. Zwitterionic surfactants can be best illustrated by betaines and sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of suitable amphoteric and zwitterionic surfactants include the alkali metal, alkaline earth metal, ammonium or substituted ammonium salts of alkyl amphocarboxyglycinates and alkyl amphocarboxypropionates, alkyl amphodipropionates, alkyl monoacetate, alkyl diacetates, alkyl amphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Particularly useful amphoteric surfactants include both mono and dicarboxylates such as those of the formulae:

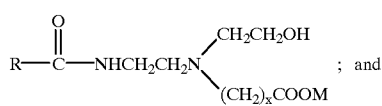

(I)

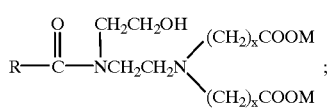

(II)

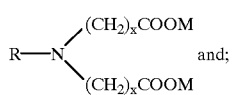

(III)

and;

wherein R is an alkyl group of 6–20 carbon atoms, x is 1 or 2 and M is hydrogen or sodium. Mixtures of the above structures are particularly preferred.

Other amphoteric surfactants can be illustrated by the following formulae:

Alkyl betaines

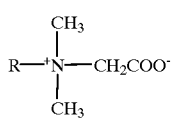

(IV)

Amidopropyl betaines

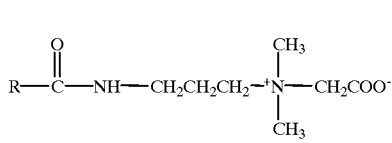

(V)

Alkyl sultaines

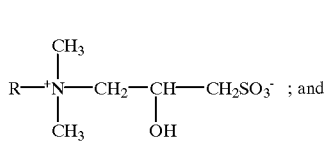

(VI)

Alkyl amidopropylhydroxy sultaines

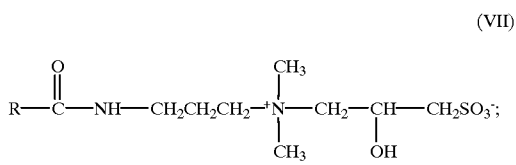

(VII)

wherein R is an alkyl group of 6–20 carbon atoms.

Of the above amphoteric surfactants, particularly preferred are compounds wherein the alkyl group is derived from natural sources such as coconut oil or is a lauryl group. In reciting a carbon chain length range, it is intended to include groups such as coco which are naturally derived materials which have various specific chain lengths or an average chain length within the range.

Commercially useful and preferred amphoteric surfactants include (as sodium salts): cocoamphoacetate (sold under the trademarks MIRANOL® CM CONC. and MIRAPON® FA, and MIRANOL® ULTRA C-32 (preferred).

cocoamphodiacetate (sold under the trademarks MIRANOL® C2M CONC. and MIRAPON® FB), cocoamphopropionate (sold under the trademarks MIRANOL® CM-SF CONC. and MIRAPON® FAS), cocoamphodipropionate (sold under the trademarks MIRANOL® C2M-SF and MIRANOL® FBS), lauroamphoacetate (sold under the trademarks MIRANOL® HM CONC. and MIRAPON® LA), lauroamphodiacetate (sold under the trademarks MIRANOL® H2M CONC. and MIRAPON® LB), lauroamphodipropionate (sold under the trademarks MIRANOL® H2M-SF CONC. AND MIRAPON® LBS), lauroamphodiacetate obtained from a mixture of lauric and myristic acids (sold under the trademark MIRANOL® BM CONC.), and cocoamphopropyl sulfonate (sold under the trademark MIRANOL® CS CONC.).

Somewhat less preferred are:

caproamphodiacetate (sold under the trademark MIRANOL® S2M CONC.), caproamphoacetate (sold under the trademark MIRANOL® SM CONC.), caproamphodipropionate (sold under the trademark MIRANOL® S2M-SF CONC.), and stearoamphoacetate (sold under the trademark MIRANOL® DM).

As used herein the term "ampho" is intended to refer to a structure derived from imidazoline chemistry. Various structures have been assigned to these products and the following are representative (x is as defined hereinbefore):

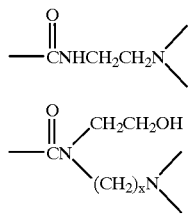

The quench liquid can also contain as the sole surfactant an anionic surfactant or the anionic surfactant can be coblended with an amphoteric surfactant during the quenching or after quenching.

Anionic Surfactants

Anionic surfactant detergents which may be included in the quench liquid used in the invention are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants.

Anionic surfactant detergents which may be included in the quench liquid used in the invention are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants.

Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants that can be mentioned include alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated deritives, acyl isethionates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of EO and/or PO, preferably EO.

Specific anionic surfactants which may be selected include linear alkyl benzene sulfonates such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof. Particularly preferred sulfonate salt is sodium dodecylbenzene sulfonate. Such chemicals have been sold under the trade name Biosoft B100 by Stepan Chemicals of Northfield, Ill. Other anionic surfactants include polyethoxylated alcohol sulfates, such as those sold under the trade name Neodol 25-3S by Shell Chemical Company. Examples of other anionic surfactants are provided in U.S. Pat. Nos. 3,976,586 and 5,415,810. To the extent necessary, these patents are expressly incorporated herein by reference.

In addition to the amphoteric and/or anionic surfactants, the quench liquid used in the process of the invention can optionally comprise one or more of a nonionic or cationic surfactants as well as other optional ingredients.

Nonionic Surfactants

The quench liquid of the invention can optionally also include one or more nonionic surfactants. The nonionic surfactant(s) is not critical and may be any of the known nonionic surfactants which are generally selected on the basis of compatibility, effectiveness and economy.

Examples of useful nonionic surfactants include condensates of ethylene oxide with a hydrophobic moiety which has an average hydrophilic lipolytic balance (HLB) between about 8 to about 16, and preferably between about 10 and about 12.5. The surfactants include the ethoxylated primary or secondary aliphatic alcohols having from about 8 to about 24 carbon atoms, in either straight or branch chain configuration, with from about 2 to about 40, and preferably between about 2 and about 9 moles of ethylene oxide per mole of alcohol.

Other suitable nonionic surfactants include the condensation products of from about 6 to about 12 carbon atoms alkyl phenols with about 3 to about 30, and preferably between about 5 to about 14 moles of ethylene oxide. Examples of such surfactants are sold under the trade names Igepal CO 530, Igepal CO 630, Igepal CO 720 and Igepal CO 730 by Rhône-Poulenc Inc. Still other suitable nonionic surfactants are described in U.S. Pat. No. 3,976,586 which, to the extent necessary, is expressly incorporated herein by reference.

Cationic Surfactants

Many cationic surfactants are known in the art and almost any cationic surfactant having at least one long chain alkyl group of about 10 to 24 carbon atoms is suitable for optional use in the present invention. Such compounds are described in "Cationic Surfactants", Jungermann, 1970, incorporated herein by reference.

Specific cationic surfactants which can be used as surfactants in the invention are described in U.S. Pat. No. 4,497,718, incorporated herein by reference.

As with the nonionic and anionic surfactants, the compositions the invention may use cationic surfactants alone but preferably in combination with other surfactants as is known in the art. The composition of the invention can contain any useful amount but preferably up to about 20% by weight of surfactant actives based on the total surfactant actives weight in the quench liquid. Of course, the composition may contain no cationic surfactants at all.

pH Adjusting Chemicals pH adjusting chemicals such as acids, bases and buffers can be added to the quench liquid. Preferred pH adjusting chemicals include lower alkanolamines such as monoethanolamine (MEA) and triethanolamine (TEA). Sodium hydroxide solutions may be utilized as an alkaline pH adjusting agent. These solutions further function to neutralize acidic materials that may be present. Mixtures of more than one pH adjusting chemical can also be utilized.

Optional Ingredients

In addition to essential ingredients described hereinbefore, the quenching liquid of the present invention can also contain a series of optional ingredients which are used for known functionality at conventional levels.

The quenching liquid of the invention can contain phase regulants (well known liquid detergent technology). These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Detergent hydrotropes could also be included. Examples of these hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzene sulfonic acids.

Other supplemental additives include defoamers such as high molecular weight aliphatic acids, especially saturated fatty acids and soaps derived from them, dyes and perfumes; fluorescent agents or optical brighteners; anti-redeposition agents such as carboxymethyl cellulose and hydroxypropylmethyl cellulose; suspension stabilizing agents and soil release promoters such as copolymers of polyethylene terephthalate and polyoxyethylene terephthalate; antioxidants; softening agents and anti-static agents; photo activators and preservatives; polyacids, suds regulators, opacifiers, bacteriacide, and the like. Suds regulants can illustrated by alkylated polysiloxanes and opacifiers can be illustrated by polystyrene; bactericide can be illustrated by butylated hydroxytoluene.

Although not required, an inorganic or organic builder may optionally be added in small amounts to the final composition. Examples of inorganic builders include water-soluble alkali metal carbonates, bicarbonates, silicates and crystalline and amorphous alumino silicates. Examples of organic builders include the alkali metal, alkaline metal, ammonium and substituted ammonium polyacetates, carboxylates, polycarboxylates, polyacetyl, carboxylates and polyhydroxy sulfonates. One example of a commonly used builder is sodium citrate.

The optional ingredients, pH adjusting chemicals and optional surfactants can be added to the quenching liquid before, during or after quenching as desired or as practical. Blends can be made directly for sale or for compounding to meet the needs of the user.

The molten reaction mixture is added to the quench liquid at a rate sufficient to effectively cool the reaction mixture beneath the degradation temperature without over heating the quench liquid. Rate of addition, quantity, heat transfer capabilities as well as the total solids desired in the final product will control and these can be readily determined by one of ordinary skill in the art.

Quenching is conducted using good chemical manufacturing techniques. The molten reaction product is preferably transferred directly to a quench vessel containing the quench liquid but can be conducted through heated piping to maintain the reaction product in molten condition. The quench vessel is preferably equipped with an agitator and a cooling jacket. While a pressurized vessel could be use, this would require a pump to overcome the difference in pressure between the reaction vessel and the quench vessel while maintaining molten flow. The quench vessel is preferably equipped with a condensation means for condensing the water evaporated from the quench liquid during quenching. The condensate is preferably reintroduced into the quench liquid.

The molten material being quenched generally can contain from about 80% to about 95%, generally around 90%, actives, the remainder of the solids being impurities and reactants. The amount of actives depends on the efficiency of fatty acid removal from the reaction mixture. The molten material is added to sufficient quenching liquid to reduce the temperature of the reaction mixture below the decomposition temperature of the reaction product. Larger amounts of quench liquid can be desirable to absorb more heat. The amount of reaction product quenched is not a function of the degree of solubility of the reaction product in the quenching liquid. The amount of reaction product quenched could be above or below the solubility limit of the reaction product in the quenching liquid.

It is preferred that the total solids in the quenching liquid after quenching (not including solids added after quenching is complete) not exceed about 60%, preferably about 50% and more preferably about 45%. Included in the solids are the reaction product, the amphoteric or anionic surfactant, the optional surfactants, and the remaining optional ingredients including the pH adjusting chemicals. The ratio of reaction product to amphoteric and/or anionic surfactant can be expressed as ranging from about 85%–!5% reaction product to about 15% to about 85% amphoteric and/or anionic surfactant based on solids. It is preferable to use from about 40% to about 60% and from about 60% to about 40% and more preferably about 50% to about 50% reaction product to amphoteric and/or anionic surfactant.

When using a blend of amphoteric and anionic surfactants in the quench liquid, one can use from a negible amount of amphoteric surfactant to slightly less than 100% with the complementary ranges for the anionic surfactant. It is preferable to use from about 30% to about 70% amphoteric surfactant to about 70% to about 30% anionic surfactant on a solids basis and more preferably from about 45% to about 55% amphoteric surfactant to about 55% to about 45% anionic surfactant on a solids basis.

The nonionic surfactant based on total solids in the quenching liquid should not exceed about 20%; the cationic surfactant not more than about 10% of the solids and the optional ingredients not more than 10% of the total solids.

After quenching, the quenched material can be cooled and used as is or further purified such as by redissolving in a lower aliphatic alcohol, e.g., isopropanol. The product can be a pumpable liquid or a paste depending on the concentration of the ingredients. Higher levels of acyloxyalkane sulfonate lead to gels so that it may be desirable to use lower levels to prepare pumpable products.

The blends of the invention can be used directly in various personal care and household cleaning products or blended with further ingredients as desired. By this invention, blends of ingredients can be made using the product of the invention as a base.

The present invention will be more fully illustrated in the following non-limiting examples.

EXAMPLE 1

Isopropanol purified N-oleyl N-methyl taurinate
Reaction apparatus

The reaction kettle was an oil jacketed 4 necked 2 liter resin pot having a drip tip drain. The kettle was equipped with a mechanical stirrer, thermometer, nitrogen sparge and Dean Starke trap leading to a reflux condenser. The kettle drain was connected to a 5 liter, three necked round bottom flask equipped with stirrer and reflux condenser.
Procedure The kettle was charged with 631.1 g (2.5 M) oleic acid 295.2 g (1.5 M) of 81.9% active sodium N-methyl taurinate 15.78 g sodium hypophosphite and a mixture of 10.71 g phosphorous acid and 20.27 g of 50% sodium hydroxide.

The reaction was heated to 230° C. and maintained 5 hours with stirring and nitrogen sparge. A total of 41.2 grams water was removed via the Dean Starke tube. The hot reaction mixture was slowly drained at 230° C. into the 5 liter round bottom flask containing 3 liters of isopropanol. The isopropanol was constantly agitated. The white slurry obtained was centrifuged at 1000–2000 rpm for 15 min. and the supernatant decanted. The white solid was washed with 1 liter isopropanol and recentrifuged. The solid was dried at 85° C. in a vacuum oven yielding 692.2 g of 80.1% active product.

EXAMPLE 2

Preparation of sodium N-cocoyl N-methyl taurinate

To the reaction kettle as described in Example 1 was charged 461.2 g (2.25 M) coconut fatty acid 15.8 g sodium orthophosphite and 15.8 g sodium hypophosphite The reaction kettle was heated to 200–210° C. and 380.0 grams (66.7% active) N-methyl taurine (1.56 M) was added over a 2 hour period. Water was removed during the addition. The dropping funnel was maintained at 40° C. to keep the N-methyl taurine flowable. After addition was complete, the reaction mixture was heated to 225° C. and held for 5 hours. The reaction mixture was drained into 3 liters of isopropanol. The white slurry is then filtered and washed with isopropanol to yield 582 grams of 84% active product.

EXAMPLE 3

Blends of N-cocoyl N-methyl taurinate with amphoteric surfactant can be prepared by adding the following to a 4 neck 2 liter reaction vessel as previously described:

380 g coconut fatty acid (C 108), 13.0 g sodium hypophosphite and 11.7 g sodium orthophosphite.

The reaction mixture was heated to 190–200° C. and an aqueous solution of 557 grams (37% active, 1.27 M) N-methyl taurine was added slowly over a 5 hour period. Water was removed continually. The reaction was held 3 hours at 230° C. until water evolution ceased. Excess fatty acid was removed by vacuum distillation. Activity by methylene blue titration was 85%. The molten reaction mixture was discharged via the bottom outlet into the 5 liter flask containing 1265 grams water and 1810 grams sodium cocoamphoacetate (Miranol® Ultra C-32). A comparison of the above blend and a similar blend at a different concentration prepared in like manner is shown below

TABLE I

| INGREDIENT | EXAMPLE 3 Wgt. % | EXAMPLE 4 Wgt. % |
|---|---|---|
| Sodium Cocoyl N-methyl Taurinate [Geropon TC 270 (82% Active)(100% Solids)] | 15 | 30 |

TABLE I-continued

| INGREDIENT | EXAMPLE 3 Wgt. % | EXAMPLE 4 Wgt. % |
|---|---|---|
| Water | 35 | 20 |
| Sodium Cocoamphoacetate [Ultra C-32 (30% Active)(38% Solids)] | 50 | 50 |
| Observation | Viscous Liq. | Paste |

What is claimed is:

1. A process for preparing blends comprising high active content, substantially salt free N-acyl aminoalkane sulfonate of the formula:

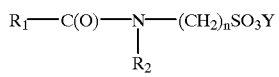

wherein $R_1$ represents a hydrocarbyl group having from about 6 to about 26 carbon atoms, $R_2$ represents hydrogen, methyl and cyclohexyl, n is an integer from 2 to 4, and Y represents alkali metal or alkaline earth metal; and amphoteric and/or anionic surfactant which comprises (a) preparing a molten reaction mixture comprising said N-acyl 2-aminoalkane sulfonate by direct amidation of an aminoalkane sulfonic acid with a fatty acid or an alkane sulfonic acid with a fatty acid amide at elevated temperatures above about 180° C., (b) quenching said molten reaction mixture in an aqueous solution comprising amphoteric and/or anionic surfactant and (c) recovering the blended product.

2. A process as recited in claim 1, wherein said elevated temperature is within the range of from about 180° to about 250° C.

3. A process as recited in claim 1, wherein said $R_1$ moiety has from 8 to 18 carbon atoms.

4. A process as recited in claim 1, wherein $R_2$ is methyl and n is 2.

5. A process as recited in claim 1, wherein said $R_1$ moiety is derived from coconut fatty acid or oleic acid or amide thereof.

6. A process as recited claim 1, wherein said amphoteric surfactant is selected from the group consisting of the alkali metal, or alkaline earth metal salts of alkylamphocarboxyglycinates, alkylamphocarboxypropionates, alkylamphodipropionates, alkylamphomonoacetates, alkylamphodiacetates, alkylamphoglycinates and alkylamphopropionates wherein the alkyl represents an alkyl group having from about 6 to about 20 carbon atoms, alkyliminoacetates, alkyliminodiacetates, alkyliminopropionates, alkyliminodipropionates and alkyl amphopropyl sulfonates wherein alkyl represents an alkyl group having between about 12 and about 18 carbon atoms, and alkyl betaines, alkylamidoalkylene betaines, alkyl sultaines and alkylamidoalkylene hydroxy sultaines wherein alkyl represents an alkyl group having from about 6 to about 20 carbon atoms and mixtures thereof and alkylene represents a chain length of from about 2 to about 4 carbon atoms.

7. A process as recited in claim 6, wherein alkyl represents a lauryl or coco group.

8. A process as recited in claim 1, wherein said amphoteric surfactant is a betaine.

9. A process as recited in claim 8, wherein said betaine is an amidopropylbetaine.

10. A process as recited in claim 8, wherein said betaine is cocamidopropylbetaine.

11. A process as recited in claim 1, wherein said amphoteric surfactant is an acylamphoacetate salt.

12. A process as recited in claim 1, wherein said quench solution after quenching comprises not more than about 60% total solids by weight and the ratio of N-acyl aminoalkane sulfonate to amphoteric and/or anionic surfactant on a solids basis ranges from about 85% to about 15% sulfonate to from about 15% to about 85% surfactant on a solids basis.

13. A process as recited in claim 1, wherein said quenching solution further includes up to about 20% by weight nonionic surfactant on a solids basis.

14. A process as recited in claim 1, wherein said anionic surfactant is selected from the group consisting of water soluble salts of alkyl benzene sulfonates having between about 8 and about 22 carbon atoms in the alkyl group, alkyl ether sulfates having between about 8 and about 22 carbon atoms in the alkyl group, and alkali metal, salts of organic sulfuric reaction products having in their molecular structure an alkyl, or aralkyl group containing from about 8 to about 22 carbon atoms and a sulfonic or sulfuric acid ester group and mixtures thereof.

15. A process as recited in claim 1, wherein said anionic surfactant is selected from the group consisting of linear sodium and potassium alkyl ether sulfates that are synthesized by sulfating a higher alcohol having between about 8 and about 22 carbon atoms and having from about 2 to about 9 moles of ethylene oxide and alkyl benzene sulfonates in which the alkyl group contains between about 9 and about 15 carbon atoms, and mixtures thereof.

16. A process as recited in claim 1, wherein said anionic surfactant is selected from the group consisting alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated deritives, acyl isethionates, fatty acid soaps, collagen hydrosylate derivatives, sulfoacetates, acyl lactates, aryloxide disulfonates, sulfosucinamides, naphthalene-formaldehyde condensates and the like wherein aryl groups include one and two rings, alkyl includes from 8 to 22 carbon atoms and the ether groups range from 1 to 9 moles of EO.

17. A process as recited in claim 13, wherein said nonionic surfactant is selected from the group consisting of condensation products of primary aliphatic alcohols having from about 8 to about 24 carbon atoms, in either straight or branch chained configuration, with from about 2 to about 40 moles of ethylene oxide per mole of alcohol and condensation products of from about 6 to about 12 carbon atoms alkyl phenols with from about 3 to about 30 moles of ethylene oxide and mixtures thereof.

18. A process as recited in claim 1, wherein said combined amphoteric and anionic surfactant comprises from about 30% to about 70% amphoteric surfactant to about 70% to about 30% by weight anionic surfactant on a solids basis.

19. A process as recited in claim 1, wherein said quench solution further comprises between about 0 and about 10% by weight of the quench liquid of supplemental additives selected from the group consisting of defoamers, dyes, perfumes, fluorescent agents, optical brighteners, antiredeposition agents, suspension stabilizing agents, soil release promoters, antioxidants, softening agents, antistatic agents, photoactivators, preservatives, inorganic builders, organic builders, additional enzymes, additional enzyme stabilizers, and mixtures thereof.

20. The product of the process of claim 1.

21. A process as recited in claim 1, wherein said N-acyl 2-aminoalkane sulfonate is present in said blend in an amount ranging from about 40% to about 60% and said amphoteric and/or anionic surfactant in an amount ranging from about 60% to about 40%.

22. A solution of N-acyl 2-aminoalkane sulfonate in aqueous amphoteric and/or anionic surfactant, wherein said N-acyl aminoalkane sulfonate has the formula:

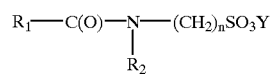

wherein $R_1$ represents a hydrocarbyl group having from about 6 to about 26 carbon atoms, $R_2$ represents hydrogen, methyl and cyclohexyl, n is an integer from 2 to 4, and Y represents alkali metal or alkaline earth metal. represents alkali metal or alkaline earth metal.

23. A solution as recited in claim 22, wherein said N-acyl aminoalkane sulfonate is N-methyl taurinate.

24. A solution as recited in claim 22, wherein said $R_1$ moiety has from 8 to 18 atoms.

25. A solution as recited in claim 22, wherein $R_2$ is methyl and n is 2.

26. -A solution as recited in claim 22, wherein said $R_1$ moiety is derived from coconut fatty acid or oleic acid or amide thereof.

27. A solution as recited in claim 22, wherein said amphoteric surfactant is selected from the group consisting of the alkali metal, or alkaline earth metal salts of alkylamphocarboxyglycinates, alkylamphocarboxypropionates, alkylamphodipropionates, alkylamphomonoacetates, alkylamphodiacetates, alkylamphoglycinates and alkylamphopropionates wherein the alkyl represents an alkyl group having from about 6 to about 20 carbon atoms, alkyliminoacetates, alkyliminodiacetates, alkyliminopropionates, alkyliminodipropionates and alkyl amphopropyl sulfonates wherein alkyl represents an alkyl group having between about 12 and about 18 carbon atoms, and alkyl betaines, alkylamidoalkylene betaines, alkyl sultaines and alkylamidoalkylene hydroxy sultaines wherein alkyl represents an alkyl group having from about 6 to about 20 carbon atoms and mixtures thereof and alkylene represnts a chain length of from about 2 to about 4 carbon atoms.

28. A solution as recited in claim 27, wherein alkyl represents a lauryl or coco group.

29. A solution as recited in claim 22, wherein said amphoteric surfactant is a betaine.

30. A solution as recited in claim 29, wherein said betaine is an amidopropyletaine.

31. A solution as recited in claim 29, wherein said betaine is cocoamidopropylbetaine.

32. A solution as recited in claim 22, wherein said amphoteric surfactant is an acylamphoacetate salt.

33. A solution as recited in claim 22, wherein said quench solution after quenching comprises not more than about 60% total solids by weight and the ratio of N-acyl aminoalkane sulfonate to amphoteric and/or anionic surfactant on a solids basis ranges from about 85% to about 15% sulfonate to from about 15% to about 85% surfactant on a solids basis.

34. A solution as recited in claim 22, wherein said quenching solution further includes up to about 20% by weight nonionic surfactant on a solids basis.

35. A solution as recited in claim 34, wherein said nonionic surfactant is selected from the group consisting of condensation products of primary aliphatic alcohols having from about 8 to about 24 carbon atoms, in either straight or branch chained configuration, with from about 2 to about 40 moles of ethylene oxide per mole of alcohol and condensation products of from about 6 to about 12 carbon atoms alkyl phenols with from about 3 to about 30 moles of ethylene oxide and mixtures thereof.

36. A solution as recited in claim 22, wherein said anionic surfactant is selected from the group consisting of water soluble salts of alkyl benzene sulfonates having between about 8 and about 22 carbon atoms in the alkyl group, alkyl ether sulfates having between about 8 and about 22 carbon atoms in the alkyl group, and alkali metal salts of organic sulfuric reaction products having in their molecular structure an alkyl, or aralkyl group containing from about 8 to about 22 carbon atoms and a sulfonic or sulfuric acid ester group and mixtures thereof.

37. A solution as recited in claim 22, wherein said anionic surfactant is selected from the group consisting of linear sodium and potassium alkyl ether sulfates that are synthesized by sulfating a higher alcohol having between about 8 and about 22 carbon atoms and having from about 2 to about 9 moles of ethylene oxide and alkyl benzene sulfonates in which the alkyl group contains between about 9 and about 15 carbon atoms, and mixtures thereof.

38. A solution as recited in claim 22, wherein said anionic surfactant is selected from the group consisting of alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated derivatives, acyl isethionates, fatty acid soaps, collagen hydrosylate derivatives, sulfoacetates, acyl lactates, aryloxide disulfonates, sulfosucinamides, naphthaleneformaldehyde condensates and the like wherein aryl groups include one and two rings, alkyl includes from 8 to 22 carbon atoms and the ether groups range from 1 to 9 moles of EO.

39. A solution as recited in claim 22, wherein said combined amphoteric and anionic surfactant comprises from about 30% to about 70% amphoteric surfactant to about 70% to about 30% by weight anionic surfactant on a solids basis.

40. A solution as recited in claim 22, wherein said solution further comprises between about 0 and about 10% by weight of the quench liquid of supplemental additives selected from the group consisting of defoamers, dyes,, perfumes, fluorescent agents, optical brighteners, antiredeposition agents, suspension stabilizing agents, soil release promoters, antioxidants, softening agents, antistatic agents, photoactivators, preservatives, inorganic builders, organic builders, additional enzymes, additional enzyme stabilizers, and mixtures thereof.

41. A solution as recited in claim 22, wherein said N-acyl 2-aminoalkane sulfonate is present in said blend in an amount ranging from about 40% to about 60% and said amphoteric and/or anionic surfactant in an amount ranging from about 60% to about 40%.

* * * * *